United States Patent
Kumar et al.

(10) Patent No.: US 11,273,100 B2
(45) Date of Patent: *Mar. 15, 2022

(54) INFUSION BAG OF MIDAZOLAM FOR INTRAVENOUS USE

(71) Applicant: Sun Pharmaceutical Industries Limited, Maharashtra (IN)

(72) Inventors: Samarth Kumar, Baroda (IN); Maheshkumar Parasmal Soni, Baroda (IN); Nishit Patel, Baroda (IN); Prashant Kane, Baroda (IN); Subhas Balaram Bhowmick, Baroda (IN)

(73) Assignee: SUN PHARMACEUTICAL INDUSTRIES LIMITED, Maharashtra (IN)

(*) Notice: Subject to any disclaimer, the term of this patent is extended or adjusted under 35 U.S.C. 154(b) by 0 days.

This patent is subject to a terminal disclaimer.

(21) Appl. No.: 16/796,292

(22) Filed: Feb. 20, 2020

(65) Prior Publication Data
US 2020/0268606 A1 Aug. 27, 2020
US 2021/0369565 A9 Dec. 2, 2021

(30) Foreign Application Priority Data
Feb. 22, 2019 (IN) .............................. 201921006935

(51) Int. Cl.
*A61J 1/14* (2006.01)
*A61J 1/10* (2006.01)
*A61K 31/55* (2006.01)
*A61K 47/02* (2006.01)

(52) U.S. Cl.
CPC .............. *A61J 1/1468* (2015.05); *A61J 1/10* (2013.01); *A61J 1/1475* (2013.01); *A61K 31/55* (2013.01); *A61K 47/02* (2013.01)

(58) Field of Classification Search
CPC .................................. A61J 1/10; A61J 1/1468
See application file for complete search history.

(56) References Cited

U.S. PATENT DOCUMENTS

2019/0388432 A1* 12/2019 Dusci .................. A61K 9/0019

FOREIGN PATENT DOCUMENTS

| EP | 2992869 A1 | 3/2016 |
|---|---|---|
| WO | 2017013677 A1 | 1/2017 |
| WO | 2017094029 A2 | 6/2017 |

OTHER PUBLICATIONS

Roche Hypnovel Product of information, 2007.*
Search Report and Written Opinion received in a International Application No. PCT/IB2020/051446 dated Jun. 4, 2020, 12 pages.
Anonymous, "Midazolam Injection Midazolam 1 mg/ml and 5 mg/ml Injection", Feb. 2, 2018, Compatibility with Infusion Solutions, 26 pages.
Pfizer Canada Inc., "Product Mongraph Midazolam Injection USP", Oct. 25, 2017, 39 pages.
M. Gerecke, "Chemical Structure and Properties of Midazolam Compared With Other Benzodiazepines", 1983. Br. J. clin. Pharmac. (1983), 16, 11S-16S. pp. 1-6.
Nunez, Pedro S, Ohlsson, Pelle D, Ordeig, Olga and Kutter, Jo¨rg P, "Cyclic Olefin Polymers; Emerging Materials for Lab-On-A-Chip Applications", Aug. 2010. https://www.researchgate.net/publication/225156790. pp. 1-18.
Hagan, Robert L, Jacobs, L. Frank III, Pimsler Meade and Merritt Gerald J. "Stability of Midazolam Hydrochloride In 5% Dextrose Injection or 0.9% Sodium Chloride Injection Over 30 Days", Nov. 1993. Am J Hosp Pharm. vol. 50.
Karlage, Kelly, Earhart, Zachary, Green-Boesen, Kelly and Myrdal, Paul B. "Stability of Midazolam Hydrochloride Injection 1-mg/ml Solutions in Polyvinyl Chloride and Polyolefin Bags", Aug. 15, 2011. Am J Health-Syst Pharm. vol. 68.
Mcmullin, Troy S, Burns Schaiff, Robyn A and Dietzen, Dennis J. "Stability of Midazolam Hydrochloride in Polyvinyl Chloride Bags Under Fluorescent Light", Sep. 15, 1995. American Society of Health-System Pharmacists, Inc. vol. 52.
Palva, et al., Clinical Trial Int Pharmacopsychiatry, 1979, 14:4:190-8 (Abstact).

* cited by examiner

Primary Examiner — Rei Tsang Shiao
(74) Attorney, Agent, or Firm — Blank Rome LLP

(57) ABSTRACT

The invention relates to an infusion container comprising a sterile, ready-to-use, stable aqueous solution of Midazolam or a pharmaceutically acceptable salt thereof, suitable for direct intravenous infusion to a patient in need thereof. The invention also relates to a novel infusion container having plurality of ports that is suitable for delivering or receiving a sterile fluid, such as the said stable aqueous solution of Midazolam or a pharmaceutically acceptable salt thereof.

19 Claims, 11 Drawing Sheets

INFUSION BAG OF MIDAZOLAM FOR INTRAVENOUS USE

FIELD OF THE INVENTION

The present invention relates to a sterile, ready-to-use infusion container comprising a stable aqueous solution of Midazolam or a pharmaceutically acceptable salt thereof, suitable for intravenous infusion. The invention also relates to a novel construction of an infusion bag having plurality of ports for delivering or receiving sterile fluid that is suitable for the said stable aqueous solution of Midazolam or a pharmaceutically acceptable salt thereof.

BACKGROUND OF THE INVENTION

Midazolam is a white to light yellow crystalline compound, insoluble in water. The hydrochloride salt of Midazolam is a water soluble benzodiazepine. Chemically, Midazolam hydrochloride is 8-chloro-6-(2-fluorophenyl)-1-methyl-4H-imidazo [1, 5-a] [1, 4] benzodiazepine hydrochloride. It is a short-acting benzodiazepine central nervous system (CNS) depressant and is generally administered alone or in combination with second medicament for e.g. morphine, atropine, scopolamine, mepiridine.

Midazolam is used via intravenous administration to treat or as a supportive medication such as preoperative anxiolysis, sedation or amnesia, prior to or during diagnostic, therapeutic or endoscopic procedures such as bronchoscopy, gastroscopy. Also it is used as an anaesthetic in cystoscopy, coronary angiography, cardiac catheterization, oncology procedures, radiologic procedures, suture of lacerations and other procedures either alone or in combination with other CNS depressants. It can be used for induction of general anaesthesia before administration of other anaesthetic agents. It can also be used as a component of intravenous supplementation of nitrous oxide and oxygen. It may further be used for sedation of intubated and mechanically ventilated patients as a component of anaesthesia or during treatment in a critical care setting. It is important to note that a mixture of Midazolam solution with other premeditations like morphine sulphate, mepiridine, atropine sulphate or scopolamine before administration is also prescribed.

Currently Midazolam is marketed at concentration of 5 mg/ml (2 ml and 10 ml ampoules) or 2 mg/ml (5 ml ampoules) which exceeds the dose required for most patients. For continuous infusion, high strength Midazolam formulations are diluted at a concentration of 0.5 mg/ml using 5% dextrose in water or 0.9% sodium chloride. It is also extremely important that no microbial contamination occur during this manipulation and the sterile nature of the product is preserved. Any deviation from recommended sterile techniques poses a risk to the safety of patient. Moreover, manual manipulations such as steps of reconstitution, dilution and incorporation into a sterile, aqueous vehicle suitable for intravenous infusion can result in the wrong dose being administered or even in the error of infusing different drugs in cases where the patient is prescribed combination or sequential therapy with multiple drugs. The National Reporting and Learning Service received 498 patient safety incidents between November 2004 and November 2008 where the dose prescribed or administered to the patient was inappropriate, and three incidents resulted in death. Till date, there is no single intravenous dosage form that provides a sterile, ready to use stable, liquid formulation of Midazolam that can be administered without any manipulation to a patient in need thereof, thereby avoiding a compromise with the sterility, an error in dosing accuracy and/or in medicament preparation etc. This necessitates the need of a sterile, ready to use infusion container comprising a stable, liquid formulation of Midazolam which can be administered to a patient in need thereof without deviation or manipulations and while preserving the sterility of the product, and also with a provision of mixing other medicaments for combination of sequential therapy, if needed.

There are also reports on Midazolam getting adsorbed onto the wall of the body of the plastic container in which it is stored, particularly polypropylene plastic containers. In 1993, Hagan et al. Am J Hosp Pharma. 1993; 50:2379-81, studied the stability of Midazolam hydrochloride 0.5 mg/ml, diluted with 5% dextrose solution and 0.9% sodium chloride in polyolefin bags. It was found that diluted preparations were stable over a period of 30 days when stored in dark at room temperature. Similarly, Karlage et al. 2011 Am J Health Syst Pharm. 2011; 68:1537, studied stability of Midazolam hydrochloride 1 mg/ml solution diluted with 5% dextrose in polyvinyl chloride and polyolefin bags. The study concluded that the diluted solution remained stable for about 27 days in both type of bags, regardless of storage conditions. McMullin et al., 1985 Am J Health Syst Pharm. 1995; 52:2018-2020, also studied stability of Midazolam 1 mg/ml in 0.9% sodium chloride, and filled in polyvinyl chloride bags under fluorescent light and reported about 10 days of stability stored at room temperature. However, there is no disclosure or suggestion in the art for a long term stability of Midazolam solution formulations in a sterile, ready-to use infusion container. Further, the present inventors while testing the stability of Midazolam hydrochloride solution in various types of infusion containers, also witnessed the problem of the adsorption of Midazolam on the wall of such containers. It was also found that the problem is concentration dependent i.e. more the solution in dilute form, more is the adsorption of Midazolam on the wall of the container, particularly when the container is a plastic infusion bag and it has been subjected to sterilization by autoclaving. This problem was found to be aggravating with increasing temperature.

In the present invention, the inventors have overcome multiple problems of prior art, such as providing a sterile, ready-to-use infusion container comprising a stable, aqueous solution of Midazolam hydrochloride, which can be administered to a patient without any manipulations and without compromising the sterility of the product. The inventors have also stabilized the formulation by designing an innovative infusion container which not only solves the problems associated with physico-chemical stability of Midazolam or a salt thereof, but also allows ease of administration of a second sterile fluid, if needed. The invention further provides a method of treating a disease or a condition or providing a supportive medication, by intravenously administering the sterile aqueous solution of Midazolam from the said infusion container, without any intermediate step(s) of dilution/reconstitution or any other type of manipulation(s) that may otherwise compromise the sterility of the solution in the infusion container or may cause an error in dosing to a patient in need thereof. The said infusion container in the preferred embodiments on the invention may have two ports. This unique feature of having two ports in the infusion bag allows simultaneous or sequential administration of a second sterile fluid, with or without a second medicament. Most importantly, the ready to use, stable liquid formulation of Midazolam hydrochloride in an infusion container according to the present invention can be terminally sterilized.

SUMMARY OF THE INVENTION

The present invention provides a sterile, ready-to-use, infusion container comprising a body filled with a stable, aqueous solution of Midazolam or a pharmaceutically acceptable salt thereof. The aqueous solution or formulation of Midazolam in an infusion container according to the present invention remains stable for a long time at different storage conditions, including after terminal sterilization by autoclaving at 121° C. for 15 minutes. Such terminally sterilized ready to use, stable aqueous formulation of Midazolam neither shows the presence of any sub-visible particles (Nylon particles) nor an adsorption of Midazolam on the inner walls of the body of infusion container, immediately after preparation as well as during long term storage, with or without terminal sterilization by autoclaving.

In one aspect, the present invention provides a sterile, ready-to-use infusion container comprising a stable, aqueous solution of Midazolam comprising:
  a. Midazolam or a pharmaceutically acceptable salt thereof;
  b. A tonicity adjusting agent;
  c. A pH adjusting agent; and
  d. water for injection.
  In a preferred embodiment, the said aqueous solution comprises 0.1 mg/ml to 2 mg/ml, and preferably 0.5 mg/ml to 1.0 mg/ml of Midazolam or a base equivalent concentration of a pharmaceutically acceptable salt thereof.
  In another preferred embodiment, the said aqueous solution has a pH of 3.0 to 4.5, more preferably 3.0 to 4.0, and most preferably 3.4±0.2.
  In another preferred embodiment, the tonicity adjusting agent in the said aqueous solution is Sodium chloride.
  In another preferred embodiment, the present invention provides a sterile, ready-to-use infusion container comprising:
  a) a body filled with about 80 ml to about 500 ml of a stable, aqueous solution of Midazolam or a pharmaceutically acceptable salt thereof, and
  b) one or more tubes fixed to the body of the container.
  In a more preferred embodiment, the container comprises at least two tubes fixed to the body of the container wherein one of the at least two tubes is fitted to an outlet port which is designed to attach to a sterile infusion set, and another tube is fitted to an inlet port which is designed to receive a sterile fluid which is with or without a medicament other than Midazolam.

In one embodiment, the infusion container is a rigid, semi-rigid or a flexible container. Preferably, the infusion container is a flexible infusion bag. More preferably, the wall of the body of the said flexible infusion bag comprises at least two layers wherein the innermost layer is made-up of a Cyclo-olefin polymer or a Cyclo-olefin co-polymer. In one of the most preferred embodiments, the wall of the body of the said flexible infusion bag comprises three layers wherein the outermost layer is made-up of Polypropylene (PP), middle layer is made-up of linear low-density Polyethylene (LDPE), and the innermost layer is made-up of a Cyclo-olefin polymer or a Cyclo-olefin co-polymer.

In another specific aspect, the present invention provides a method of treating a disease or a condition or providing a supportive medication, by intravenously administering to a patient in need thereof, the stable aqueous solution of Midazolam or a pharmaceutically acceptable salt thereof, from a sterile, ready-to-use infusion container.

In one more aspect, the invention provides use of a sterile, ready-to-use infusion container comprising a stable, aqueous solution of Midazolam or a pharmaceutically acceptable salt thereof for treating a disease or a condition or for providing a supportive medication, by intravenously administering to a patient in need thereof.

DETAILED DESCRIPTION

Figure 1:
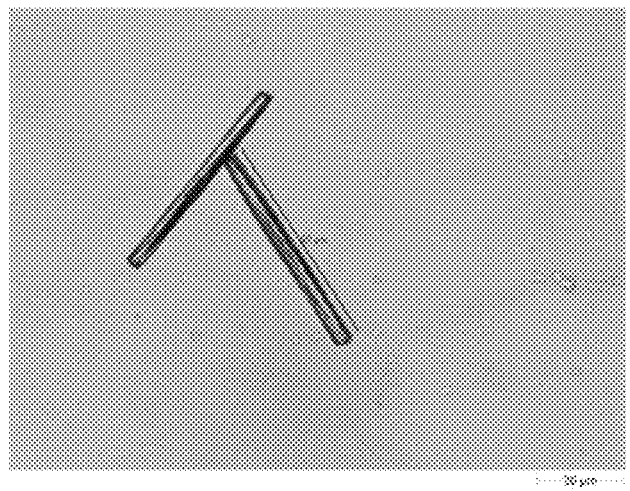
FIG. 1: Rod shaped sub visible particles identified as Nylon oligomers in in Midazolam ready to infuse formulation filled in IC-H-AE-1 and IC-S infusion containers using Morphology with Raman by G3 ID (Example 3)

The phrase 'autoclavable and stable' or "autoclaved and stable" are used herein as interchangeable and means that by autoclaving there is no substantial change in the content or assay percentage of Midazolam during any of the stages of preparation and/or storage of the infusion container, throughout the shelf life period The term 'infusion container' according to the present invention refers to a container in which a solution of the medicament remains stable during preparation, during sterilization and also during storage.

The infusion container may be a rigid, semi-rigid or a flexible container. The wall of the body of the said container may comprise one or more layers, preferably at least two layers and more preferably at least three layers. In preferred embodiments, the innermost layer of the infusion container is made-up of a material that does not show any adsorption of Midazolam thereby causing no loss of potency and/or assay percentage during preparation, sterilization and during storage. One of the preferred materials for the innermost layer is Cyclo-olefin polymer or a Cyclo-olefin co-polymer. In a specific embodiment, the wall is made up of at least three layers of flexible films which are adhered, molded or sealed together by a suitable means such as heat molding, co-extrusion, and the like. All the layers are free of metal part. In preferred embodiments, the innermost layer of the wall of the body of the infusion container is made up of a polymer selected from a cyclo-olefin polymer or a cyclo-olefin co-polymer. In one embodiment the co-polymer is made-up of cyclo-olefin and olefin. The innermost layer remains in contact with the aqueous solution of Midazolam contained in the infusion container. The multi-layered infusion container may comprise other layers that may be made up of materials such as polyethylene, polypropylene, modified polyolefin-polyethylene polymers, styrene-polyolefin based polymers and block co-polymers thereof etc. Also, an adhesive layer including an adhesive resin may optionally be included between the outermost layer and the innermost layer. However, the innermost layer is always made up of a polymer selected from a cyclo-olefin polymer or a cyclo-olefin co-polymer. In one of the most preferred embodiments, the body of the container comprises at least three layers, having an outermost layer made up of Polypropylene (PP), a middle layer made up of linear low density polyethylene (LDPE) and an innermost layer made up of a cyclo-olefin polymer or a cyclo-olefin co-polymer (COP).

The infusion container of the present invention does not contain a metal. In one embodiment, the body of the infusion container is rectangular in shape and having length in the range of 150 to 250 mm and width in the range of 50 to 150 mm. In some preferred embodiments, the length is about 173 mm and the width is about 100 mm. The multi-layered wall of the body of the container has a total thickness in the range of about 150 µm to 250 µm. The infusion container has an oxygen transmission rate in the range of 600 to 1000 ml/(m$^2$·24 hr·atm) and water vapour transmission rate in the range of 1.0 to 5.0 g/m$^2$·24 hr. The volume capacity of each infusion container may range from about 50 ml to about 500 ml, preferably from about 75 ml to about 450 ml, such as for example 80, 85, 90, 95, 100, 105, 110, 115, 120, 125, 130, 135, 140, 145, 150, 6155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440 or 450 ml, more preferably from about 80 ml to 400 ml. According to preferred embodiments of the present invention, the infusion container can accommodate a volume from about 100 ml to 200 ml, preferably about 100 ml.

Figure 10:
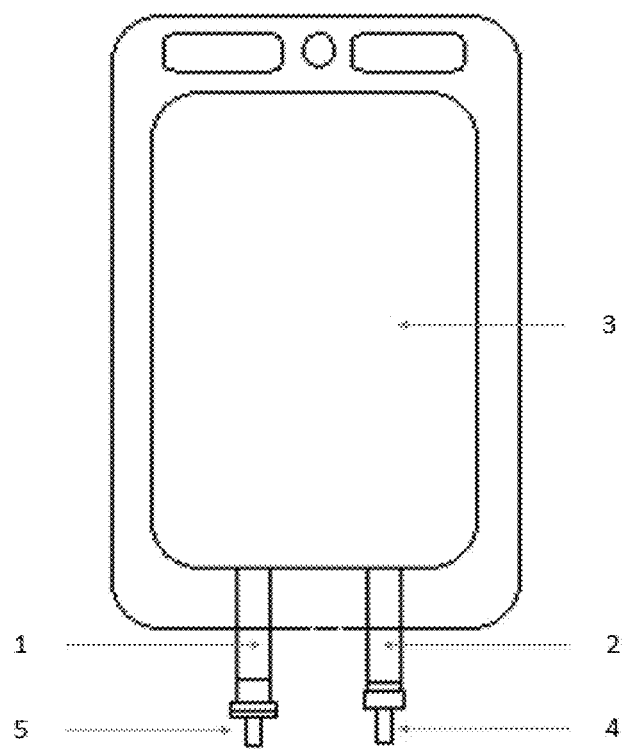
FIG. 10 illustrates different parts of the infusion container of the present invention namely: two tubes fitted to the body of the infusion container ((1) and (2)), wall of the body of the infusion container (3), an inlet port (4) and an outlet port (5).
Figure 11:
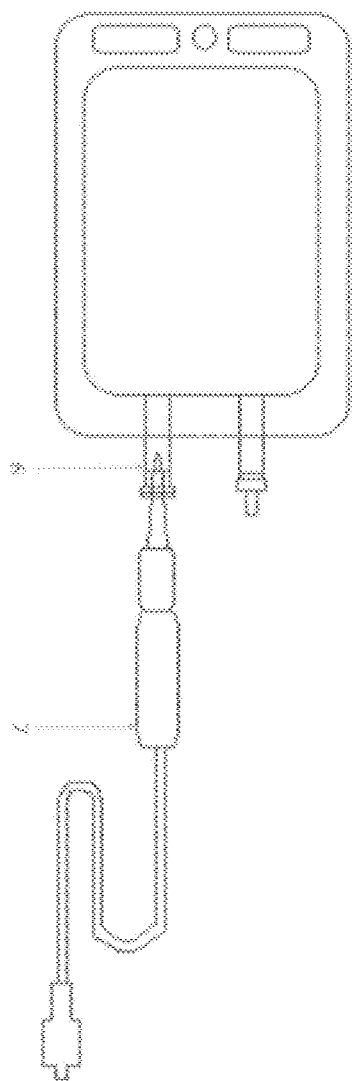
FIG. 11 represents the assembly of infusion container of the present invention wherein a spike (6) of an infusion set (7) is inserted into the outlet port of the infusion container.

The infusion container may comprise two parts, namely the body and the tubes for entry or exit of the sterile solution (See FIG. 10). The term 'outlet port' as used herein refers to a connector which is inserted into the tube. The outlet port is represented by part 5 of FIG. 10. The outlet port may have a rubber plug to provide a fluid tight closure of the passage and a lid member that clamps the periphery of the rubber plug. It is designed to attach to a sterile infusion set (7) via means such as a spike (6) that allows exit delivery of the solution from the container to the patient through the infusion set. (See FIG. 11). The term 'inlet port' as used herein refers to a connector which is inserted into one of the tubes and which is designed to receive a sterile fluid. It may have a resalable plug which provides fluid tight closure of the passage and a plastic cap that clamps the periphery of the resealable plug (See part 4 of FIG. 10). The term 'spike' as used herein refers to a cylindrical part of an infusion set (7) which has an opening and which is suitable for piercing the rubber plug of outlet port and getting connected to the outlet port so as to provide a passage way to the medicament to exit from the bag through the outlet port and the spike, into the infusion set tubing, which is connected on the other side to a needle suitable for insertion and infusion of the medicament. (See part 6 of FIG. 11).

In one embodiment, the infusion container has two tubes that are fixed to the body of the container towards one end of the container. The other end of the tubes is fixed to the ports. It is however possible to have one tube fixed with one port at one end of the container and another tube fixed to other port at another end of the container. The tube is fixed to the body of the container at one end and the other end has a provision of attachment to port which is either an inlet port or an outlet port. In one preferred embodiment, the tube is made up of three layers comprising an outer layer made up of a cyclo-olefin polymer or a cyclo-olefin co-polymer and the middle or inner layers made up of polymers like polyolefin, polypropylene, polyethylene, polystyrene etc. It is preferable that the outer layer of the tube be made up of cyclo-olefin polymer or cyclo-olefin co-polymer. In a more preferred embodiment, the tube is made up of three layers comprising Polypropylene, Hydrogenated Styrene Butadiene Copolymer (Cycloolefin co polymer) and Ethylene-vinyl acetate copolymer.

The infusion container of the present invention may optionally be overwrapped by an overwrap pouch covering the filled and sealed infusion container. Preferably the infusion container is overwrapped by an aluminium pouch.

The present invention does not include containers that are available in the form of foils which are fixed and which tapers at one side. Such types of containers are known in the art as collapsible tubes and contain a tapered shape with a tube head. These are not encompassed within the scope of the present invention. Also, the present invention does not include conventional containers such as infusion vials or ampoules, syringes, prefilled syringes, particularly those which do not provide a ready-to-use solution. The present invention further does not relate to semi-solid topical formulations (such as gel, hydrogel, emulgel, paste, cream, ointment etc.), inhalations or aerosols and/or non-aqueous formulations that are not suitable for parenteral administration.

The sterile, ready-to-use infusion container of the present invention is filled with a stable, aqueous solution of Midazolam or a pharmaceutically acceptable salt thereof, in volumes ranging from about 80 ml to about 500 ml. In one preferred embodiment, the pharmaceutically acceptable salt of Midazolam according to the present invention is a hydrochloride salt. Other non-limiting examples of the suitable salts may be maleate and lactate. The said ready-to-use, stable, aqueous solution according to the invention has a concentration ranging from about 0.05 mg/ml to about 5.0 mg/ml; preferably from about 0.1 to 2.0 mg/ml, such as for example 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9 or 2.0 mg/ml, more preferably from about 0.5 to 1.0 mg/ml, of Midazolam or a base equivalent concentration of a pharmaceutically acceptable salt thereof. In preferred embodiments, the ready-to-use, sterile, stable aqueous solution filled in the infusion container comprises a concentration in the range of about 0.5 mg/ml to about 1.0 mg/ml of Midazolam or a base equivalent concentration of a pharmaceutically acceptable salt thereof. In one of the more preferred embodiments, the sterile, ready-to-use, stable aqueous solution filled in the infusion container comprises a concentration of 1.0 mg/ml of Midazolam or a base equivalent concentration of a pharmaceutically acceptable salt thereof. In another more preferred embodiment, the sterile, ready-to-use, stable aqueous solution filled in the infusion container comprises a concentration of 0.5 mg/ml of Midazolam or a base equivalent concentration of a pharmaceutically acceptable salt thereof.

The dissolved oxygen content in the ready-to-use, sterile, stable aqueous solution of Midazolam or a pharmaceutically acceptable salt thereof, according to the present invention is 2 parts per million (ppm) or less, i.e. 0 to 2 ppm, preferably 0 to 1.0 ppm or 0.001 to 1.0 ppm more preferably 0 to 0.5 ppm, such as for example 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48 or 0.49 ppm. To achieve and maintain dissolved oxygen content in the range of 0 to 2 ppm, the aqueous solution is purged with an inert gas like nitrogen, argon or helium.

The aqueous solution of Midazolam according to the present invention is filled in the infusion container in volumes ranging from about 80 ml to about 500 ml, preferably from about 100 ml to about 400 ml, such as for example 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390 or 400 ml, more preferably from about 100 ml to 200 ml.

The aqueous solution according to the present invention may further comprise parenterally acceptable excipients such as, but not limited to, osmotic agents or tonicity adjusting agents, pH adjusting agents, buffers. In one embodiment, an osmotic agent or a tonicity adjusting agent is used to adjust the tonicity of the solution and make the solution iso-osmolar to the parenteral/plasma fluids. The osmotic agent may be selected from, but is not limited to, a group consisting of sodium chloride, potassium chloride, mannitol, sorbitol, dextrose, sucrose and the like or mixtures thereof. In a preferred embodiment, the osmotic agent or a tonicity adjusting agent is sodium chloride. Preferably, sodium chloride is used at a concentration of about 0.9% w/v.

The pH of the aqueous solution according to the present invention is in the range of about 3.0 to 4.5, such as for example 3.1, 3.2, 3.3, 3.4, 3.5, 3.6, 3.7, 3.8, 3.9, 4.0, 4.1, 4.2, 4.3, 4.4 or 4.5, preferably in the range of about 3.0 to 4.0, more preferably 3.4±0.2. The ready-to-use, sterile, stable aqueous solution having a pH in the range of 3.0 to 4.5 shows good stability. The pH of the solution may be adjusted by use of a pH adjusting agent, and optionally, if needed a buffer may be used to maintain the pH in the said range. The pH adjusting agent that may be used include, but are not limited to sodium hydroxide, potassium hydroxide, hydrochloric acid, sulphuric acid, acetic acid, sodium acetate, tartaric acid, and the like, and mixtures thereof. In one preferred embodiment, the pH adjusting agent is sodium hydroxide and hydrochloric acid.

In preferred aspects, the ready-to-use, sterile, stable aqueous solution of the invention is free of one or more chelating agents, antioxidants, stabilizers, complexing agents and/or preservatives.

The sterile infusion container of the present invention can be terminally sterilized without compromising with the stability and/or adsorption behaviour of the stable aqueous solution of Midazolam. More particularly, the infusion container is capable of maintaining the stability of the solution after terminal sterilization by autoclaving and upon storage at room temperature for a period of at least 6 months.

According to the invention, the decrease in assay of Midazolam upon autoclaving and upon storage at room temperature for a period of at least 6 months is not more than 5% by weight of labelled Midazolam content. It was also found that Midazolam solution when stored in an infusion container having innermost layer made up of polymer selected from cycloolefin polymer or cycloolefin copolymer remained stable upon long term storage with no signs of any visible particles (Nylon particles) or adsorption of Midazolam on the inner wall of infusion container, and impurities (see Table 1) also remained under pharmaceutically acceptable range.

TABLE 1

Midazolam Impurity structures

| Impurity | Structure |
| --- | --- |
| Oxide Midazolam (%) | 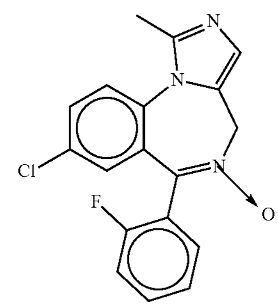 |
| 6-H Isomer (%) | 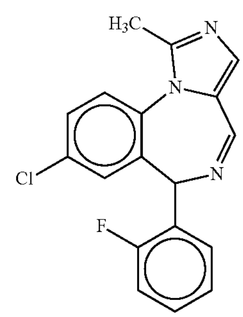 |
| Impurity H (%) | 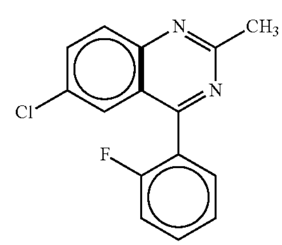 |
| Impurity F (%) | 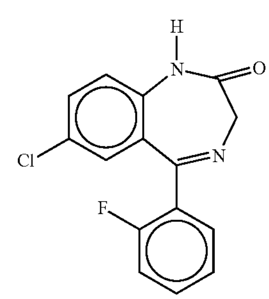 |

TABLE 1-continued

Midazolam Impurity structures

| Impurity | Structure |
|---|---|
| Midazolam Aldehyde Impurity (%) | (structure shown) |

It was also surprisingly found by the present inventors that when an infusion container made up of certain materials, which does not have a cyclo-olefin polymer or a co-polymer in contact with aqueous solution of Midazolam hydrochloride solution, such as for example infusion bags having inner layer made up of (i) low density polyethylene or (ii) polypropylene or (iii) polyolefin copolymer or (iv) ethylene propylene copolymer; there occurred a significant loss of assay percentage of Midazolam immediately after autoclaving which is undesirable. Significant loss of assay percentage of Midazolam was also observed in case of those infusion containers that have a cyclo-olefin layer as an outer layer while the innermost layer made up of some other polymer like low density polyethylene or polypropylene. From the packaging material screening study, the loss of the assay percentage of Midazolam was found to be due to adsorption of Midazolam onto the wall of the infusion container. Such a significant drop in the assay of Midazolam is further aggravated due to application of high temperature and pressure while autoclaving. It was also found by the present inventors that a material that has a cyclo-olefin polymer or a co-polymer in the innermost layer of the infusion container provides optimal solution stability with substantially no loss in assay or content of Midazolam upon autoclaving and upon long term storage (See Example 2, Table 7).

The infusion container of the present invention provides a means of direct intravenous administration of the sterile, stable aqueous solution of Midazolam or a pharmaceutically acceptable salt thereof, to the patient through the infusion container, using the outlet port fitted with a spike of an infusion set. This avoids chances of contamination of the solution while administration. In one of the most preferred embodiments, the infusion container is terminally sterilized via autoclaving at 121° C. for 15 minutes, and provides a ready-to-infuse, stable and sterile aqueous solution, that can be intravenously administered without compromising the physico-chemical stability of Midazolam or a pharmaceutically acceptable salt thereof.

In preferred embodiments, the infusion container of the present invention consists of two tubes fitted at one end of the container and having provision for attachment of two different ports, that is, the outlet port and the inlet port respectively. In a preferred embodiment, the infusion container of the present invention comprises one outlet port which is adapted for attaching to an infusion tubing of an infusion set for delivering the aqueous solution to the patient and an inlet port designed to receive a medicament to be mixed in the aqueous solution. The table below illustrates the significance of presence of two ports in the infusion bag of the present invention. It will be appreciated that the provision of administering a combination of two medicaments allows ease of delivery to the patient.

TABLE 2

Illustrative Example A

| | Midazolam infusion Container | Additional drugs for co-administration with Midazolam (filled in the infusion container through the inlet port) | | | | |
|---|---|---|---|---|---|---|
| Drug Name » | Midazolam hydrochloride (mg) | Morphine (mg) | Mepiridine (mg) | Atropine (mg) | Scopolamine (mg) | Fentanyl (mg) |
| Concentration of drug solution in mg/ml » | 1 | 0.5 | 5 | 50 | 0.4 | 0.25 | 0.05 |

| Volume (ml) of Midazolam solution in container ↓ | Amount of Midazolam (mg) | Amount of other medicaments in container (mg) | | | | |
|---|---|---|---|---|---|---|
| 100 | 100 | 50 | 30 | 50 | 2 | 0.32 | 0.025 |
| 200 | 200 | 100 | 30 | 100 | 2.5 | 0.65 | 0.05 |
| 300 | 300 | 150 | 30 | 150 | 3 | 0.65 | 0.1 |

TABLE 3

Illustrative Example B

| | Midazolam infusion container | Additional drugs for co-administration with Midazolam (filled in the infusion container through the inlet port) | | | | |
|---|---|---|---|---|---|---|
| | Midazolam hydrochloride (mg) | Cyclizine | Oxycodone hydrochloride | Hydro-morphan | Ketamine HCl | Levomepromazine hydrochloride |
| Concentration of drug solution in mg/ml » | 1 | 0.5 | 50 | 10 | 2 | 10 | 25 |

TABLE 3-continued

Illustrative Example B

| Volume (ml) of Midazolam solution in container ↓ | Amount of Midazolam (mg) | Amount of other medicaments in container (mg) | | | | | |
|---|---|---|---|---|---|---|---|
| 100 | 100 | 50 | 50 | 6 | 0.2 | 20 | 25 |
| 200 | 200 | 100 | 50 | 20 | 1 | 20 | 100 |
| 300 | 300 | 150 | 50 | 40 | 1 | 20 | 200 |

According to one embodiment, the present invention provides a method of preparing infusion container of Midazolam which includes filing a stable aqueous solution of Midazolam or a pharmaceutically acceptable salt thereof, in an infusion container, sealing the container and terminally sterilizing the filled and sealed infusion container by autoclaving or irradiation of suitable wavelength of radiation, e.g. gamma-rays. In this method the wall of infusion container has an outermost layer of polypropylene, middle layer of linear low density polyethylene and innermost layer of a cyclo-olefin polymer or a cyclo-olefin co-polymer. The infusion container also has two ports, one is an outlet port through which the solution of Midazolam is filled and the other is an inlet port which is pre-sealed. The said method comprises steps of—

(i) dissolving an osmotic agent or a tonicity adjusting agent, such as sodium chloride in water for injection having dissolved oxygen content of less than 1 ppm, (ii) adding 1% w/w hydrochloric acid to (i) and stirring, (iii) Adding Midazolam to (ii) with continuous stirring to form a uniform dispersion, (iv) adjusting the pH of resulting dispersion to 3.0±0.1 using 1% w/w hydrochloric acid and stirring to ensure complete dissolution of Midazolam, (v) adjusting the pH of bulk solution to 3.4±0.2 using 1% w/w sodium hydroxide solution, If pH goes more than the said range during pH adjustment, then again adjust it using 1% w/w Hydrochloric acid.

(vi) making up the final volume with water for injection and purging the solution with nitrogen to get dissolved oxygen content of less than 1 ppm, (vii) filtering the solution of (vi) through 0.2 micron membrane filter, (viii) filling specified volume of the aqueous solution in the body of an infusion container through an open tube fixed to the container with open outlet port, (ix) stoppering the tube with the help of an outlet port, (x) terminally sterilizing the filled and stoppered infusion container by subjecting the container to autoclaving at a temperature of 121° C. for 15 minutes, (xi) optionally, overwrapping the infusion container using a pouch and replacing the space between overwrap and infusion bag with an inert gas like nitrogen.

Hereinafter, the invention is more specifically described by way of examples. The examples are not intended to limit the scope of the invention and are merely used as illustrations.

Example 1: Formulation Development

TABLE 4

Composition

| INGREDIENTS | MG/ML | MG/ML |
|---|---|---|
| Midazolam HCl eq. to Midazolam base | 1 | 0.5 |
| Sodium Chloride | 9 | 9 |
| Hydrochloric Acid | q.s. to pH 3.4 ± 0.2 | q.s. to pH 3.4 ± 0.2 |
| Sodium Hydroxide | q.s. to pH 3.4 ± 0.2 | q.s. to pH 3.4 ± 0.2 |
| Water for Injection | q.s to 1 mL | q.s to 1 mL |

Manufacturing process: Bulk solution preparation: 80% of the batch size of water for injection (WFI) was collected at a temperature of 20° C. to 25° C. in stainless steel 316L manufacturing tank of suitable capacity. Nitrogen gas was purged to get dissolve oxygen content less than 1 mg/L (ppm), pressure of nitrogen gas and time of purging or flow rate of nitrogen gas were recorded. Sodium chloride was added and dissolved gradually followed by stirring for not less than 10 minutes to ensure complete solubilization and clarity of solution visually. While additional excipients were added as below, the purging was stopped. 1% w/w hydrochloric acid (35 mL/Kg) was added and stirred well for approximately 10 minutes. Midazolam hydrochloride was added slowly into bulk solution with continuous stirring, the dispensing container was rinsed with dissolved oxygen maintained WFI and added to the bulk solution, rinsing was repeated till all the contents are transferred. The pH was adjusted to 3.0±0.1 using sufficient quantity of 1% w/w hydrochloric acid and stirred for around 1 h after pH adjustment to ensure complete dissolution of drug, stabilization of pH and until the appearance of the solution was a clear colourless solution. The pH was adjusted at 3.4±0.2 using sufficient quantity of 1% w/w Sodium hydroxide solution, and the volume was made up with dissolved oxygen maintained WFI stored at 20° C. to 25° C. If pH goes more than the said range during pH adjustment, then again it was adjust to 3.4±0.2 using 1 w/w Hydrochloric acid". The solution was stirred for 10 minutes until a clear solution was obtained. Nitrogen was purged to get dissolve oxygen content less than 1 mg/L (ppm), and the pH was finally checked to be 3.4±0.2.

Filtration: The bulk solution was filtered through 0.2 micron Polyethersulfone (PES) membrane filter.

Filling & Stoppering: Filtered bulk solution was filled at standard fill volume in the IC-PHC infusion bag and the infusion bag was stoppered with sterile stoppers.

Terminal sterilization: The stoppered infusion bags were terminally sterilized by autoclaving at 121° C. for 15 minutes.

Over wrapping: Infusion bags were over wrapped using aluminum pouch by over wrapping machine. Optionally, the space between overwrap and bags can be replaced with the nitrogen or inert gas.

Example 2: Packaging Material and Screening

Samples were prepared as per the process described above. Filtered solution was filled into a variety of infusion containers as per the layer-wise composition given below in Table 5, and were subjected to autoclaving.

TABLE 5

Infusion bags and its layer-wise composition

| Infusion Container No. | Layer | Layer wise composition |
|---|---|---|
| IC-H-AE-1 | Outside | Polyamide 11 |
| | Tie | Modified polyolefin |
| | Inside | LLDPE |
| IC-S | Outside | CPET |
| | Tie | Functionalized ethylene alpha olefin copolymer |
| | Middle | PE |
| | Tie | SEBS |
| | Inside | EPC |
| IC-PHC | Outside | PP |
| | Middle | LLDPE |
| | Inside | COP |
| IC-MPHC | Outside | COP |
| | Middle | LLDPE |
| | Inside | PP |
| IC-MEHC | Outside | COP |
| | Middle | LLDPE |
| | Inside | LDPE |

Note:
Inside layer is the layer that comes in contact with Midazolam solution.

Abbreviations
LLDPE: Linear Low Density Polyethylene
LDPE: Low density polyethylene
EPC: Ethylene propylene copolymer
PE: Ethylene alpha olefin copolymer
CPET: Poly cyclohexane dimethylcyclohexane dicarboxylate elastomer
COP: Cyclo olefin polymer
SEBS: Styrene-ethylene-butylene-styrene block copolymer
PP: Polypropylene

TABLE 6

Stability data of Midazolam HCL Injection at different strength in autoclaved and unautoclaved conditions @ pH 3.4.

| Sr No | Bag | Concentration (mg/mL) | Autoclave Condition | Batch Number | Assay |
|---|---|---|---|---|---|
| 1 | IC-MEHC | 0.2 | Unautoclaved | 26201282PF037I | 101.13 |
| 2 | | | 121° C.-15 mins. | 26201282PF037I1 | 81.85 |
| 3 | IC-MPHC | | Unautoclaved | 26201282PF037J | 102.48 |
| 4 | | | 121° C.-15 mins. | 26201282PF037J1 | 87.83 |
| 5 | IC-PHC | | Unautoclaved | 26201282PF037K | 101.15 |
| 6 | | | 121° C.-15 mins. | 26201282PF037K1 | 99.94 |
| 7 | Glass Vial | | Unautoclaved | 26201282PF037L | 101.52 |
| 8 | | | 121° C.-15 mins. | 26201282PF037L1 | 101.13 |
| 9 | | | Unfiltered | 26201282PF037O | 101.19 |
| 10 | IC-MEHC | 0.5 | Unautoclaved | 26201282PF037E | 99.07 |
| 11 | | | 121° C.-15 mins. | 26201282PF037E1 | 84.29 |
| 12 | IC-MPHC | | Unautoclaved | 26201282PF037F | 100.25 |
| 13 | | | 121° C.-15 mins. | 26201282PF037F1 | 90.63 |
| 14 | IC-PHC | | Unautoclave | 26201282PF037G | 101.48 |
| 15 | | | 121° C.-15 mins. | 26201282PF037G1 | 100.46 |
| 16 | Glass Vial | | Unautoclaved | 26201282PF037H | 100.48 |
| 17 | | | 121° C.-15 mins. | 26201282PF037H1 | 100.71 |
| 18 | | | Unfiltered | 26201282PF037N | 99.99 |
| 19 | IC-MEHC | 1 | Unautoclaved | 26201282PF037A | 100.5 |
| 20 | | | 121° C.-15 mins. | 26201282PF037A1 | 92.31 |
| 21 | IC-MPHC | | Unautoclaved | 26201282PF037B | 101.07 |
| 22 | | | 121° C.-15 mins. | 26201282PF037B1 | 96.75 |
| 23 | IC-PHC | | Unautoclaved | 26201282PF037C | 100.21 |
| 24 | | | 121° C.-15 mins. | 26201282PF037C1 | 99.73 |
| 25 | Glass Vial | | Unautoclaved | 26201282PF037D | 101.13 |
| 26 | | | 121° C.-15 mins. | 26201282PF037D1 | 100.69 |
| 27 | | | Unfiltered | 26201282PF037M | 99.99 |

From the above study it is seen that when samples were subjected to autoclave condition at 121° C.-15 minutes, IC-MEHC and IC-MPHC bag showed substantial decreases in assay as compared to IC-PHC bag and glass vial. This suggest Midazolam hydrochloride solution is stable in the IC-PHC infusion bag and glass vial.

Figure 2:
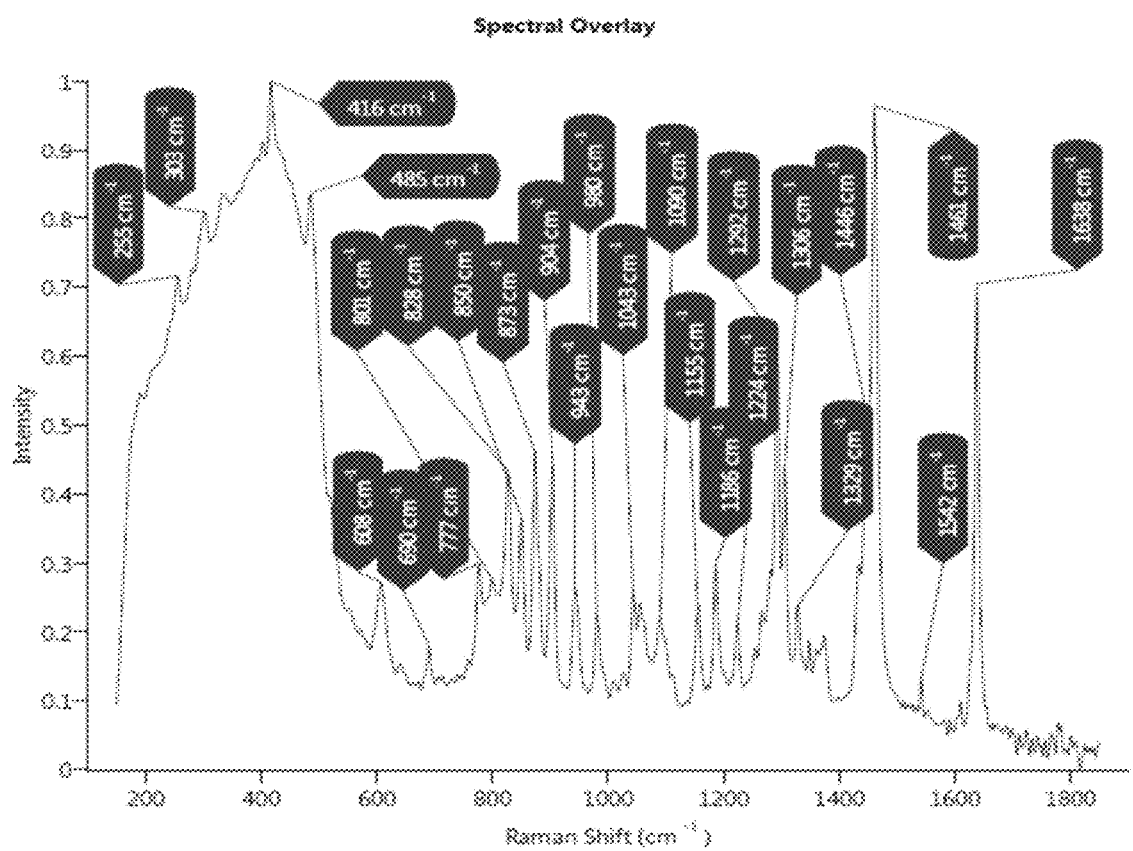
FIG. 2: Raman spectra of Monomer—Nylon 11 (Example 3)
Figure 3:
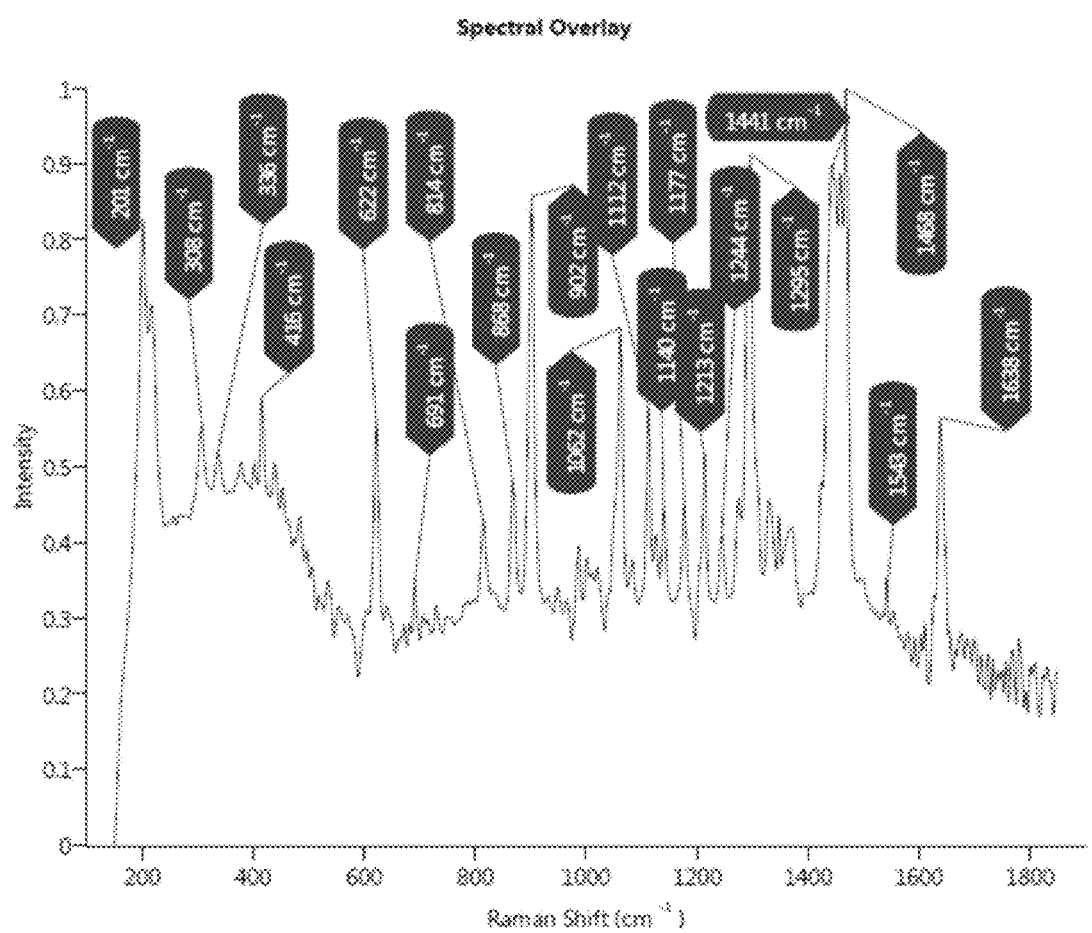
FIG. 3: Raman Spectra of Dimer—Nylon 11 (Example 3)
Figure 4:
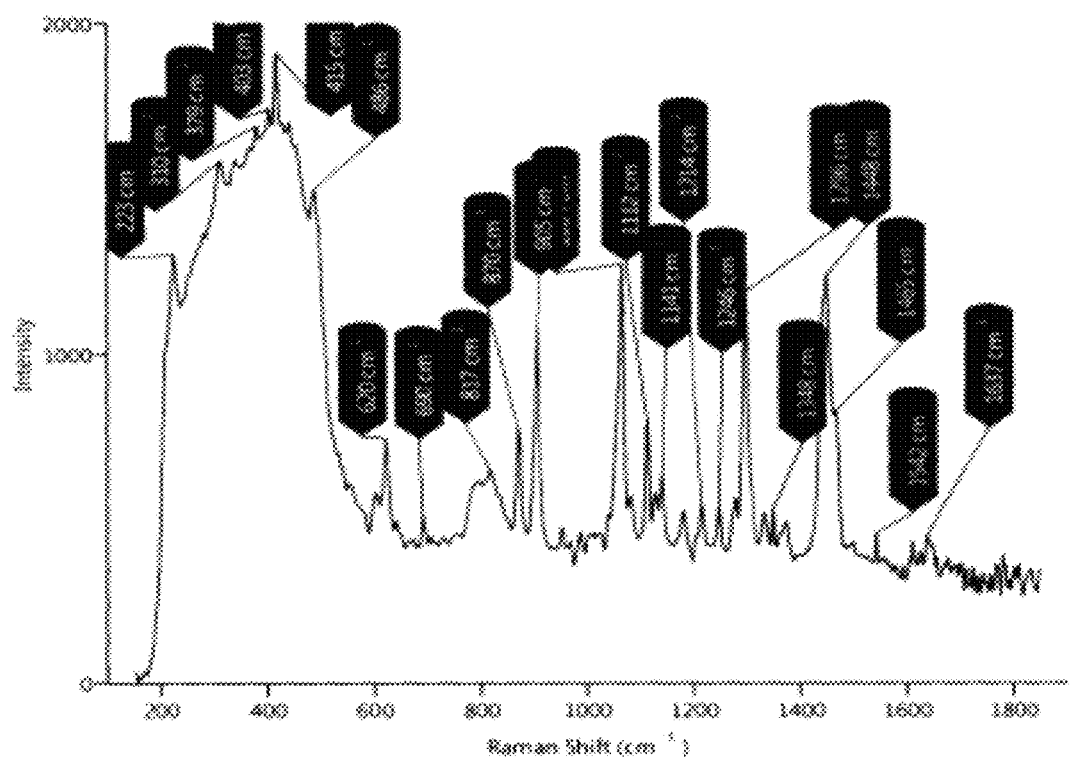
FIG. 4: Raman Spectra of particle observed in Midazolam injection sample in IC-H-AE-1 infusion containers (Example 3)

Example-3: Identification & Characterization of Sub-Visible Rode Shape Particles in Midazolam Ready to Infuse Formulation Filled in IC-H-AE-1 and IC-S Infusion Bags Using Morphology with Raman by G3 ID Method: Formulation from infusion bag was filtered through fine micron filter papers (0.2 μm PES, 47 mm). Filter paper was then evaluated for particles morphology using microscope. Further, particles containing filter paper was tapped to transfer particles on the quartz plate, and analyzed to obtain Raman spectra of identified particle.
Results: Sub visible particles were observed in IC-H-AE-1 infusion bags. Similar particles were also observed in samples of Midazolam injection in IC-H-AE-1 infusion bags. The particles were not observed in IC-S infusion bags under studied conditions. Morphology with Raman G3 ID was performed to identify these sub visible particles found in Midazolam Injection sample filled in IC-H-AE-1 infusion bags. Raman spectra obtained from rod-shape particle were compared with Raman spectra of standard of nylon oligomers (Monomer and dimer of nylon—11). The prominent peaks observed at 700-1260 cm'(functional group: C—C), 1410-1460 cm'(Functional group: CH3 & CH2 deformations), 1620-1690 $cm^{-1}$ (functional group: >C=O mixed with NH deformations) positions in particle collected from Midazolam injection filled in IC-H-AE-1 bag (FIG. 3) were similar to peaks observed in same positions in Raman spectra of Nylon standards (FIGS. 2 & 3). Presence of more prominent bands at 700-1260 $cm^{-1}$, 1410-1460 $cm^{-1}$, 1620-1690 $cm^{-1}$ position in the spectra evident the presence of Nylon in the particles obtained from Midazolam injection filled in IC-H-AE-1 bag. Thus, IC-H-AE-1 infusion bag was not found suitable for Midazolam solution. Subsequently, other infusion bags namely, IC-S infusion bag, two port sterile IC-S' infusion bags and IC-PHC infusion bags were evaluated.

Example-4: Terminal Sterilization of Midazolam Ready to Infuse Formulation Filled in Different Packaging Material Method: Midazolam formulation samples (i) autoclaved and (ii) unautoclaved, were stored in different packaging materials, i.e. glass bottle, IC-H-AE-1, IC-S, IC-S' and IC-PHC. Initial potency of Midazolam in such samples was tested using an HPLC based assay method.

Figure 5:
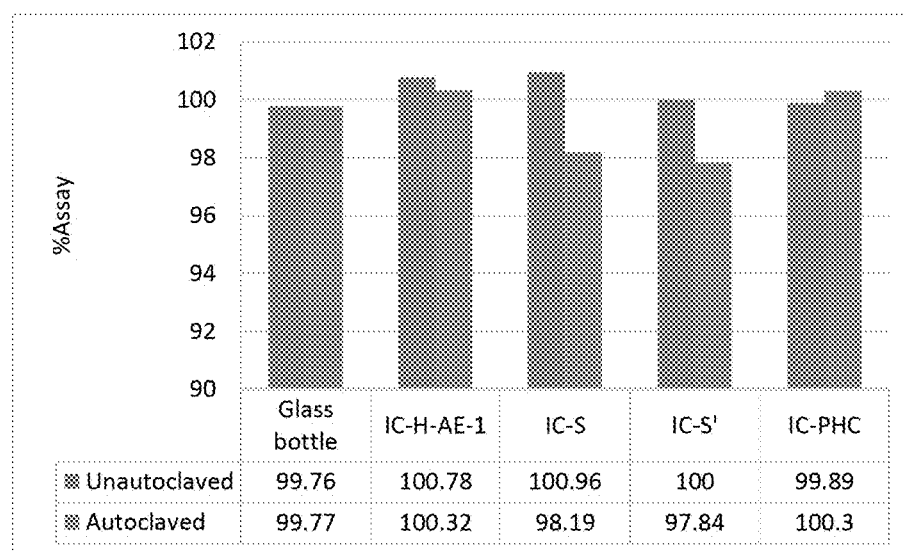
FIG. 5: Depicts no significant change in Midazolam potency in IC-PHC infusion containers (Example 4)
Unautoclaved on the left; autoclaved on the right

Discussion: Midazolam potency was found to decrease after autoclaving in IC-S and IC-S' infusion bags (FIG. 5). On the other hand, there was no significant difference between assay values of autoclaved and un-autoclaved samples of Midazolam injection in IC-PHC infusion bags. This revealed the superior behaviour of IC-PHC over other infusion bags. Potency loss was also not observed in IC-H-AE-1 infusion bags; however, because of Nylon particle leaching, these bags are not suitable. Based on the packaging material screening study (Example 2), Midazolam adsorption was observed in IC-S infusion bags.

Figure 6:
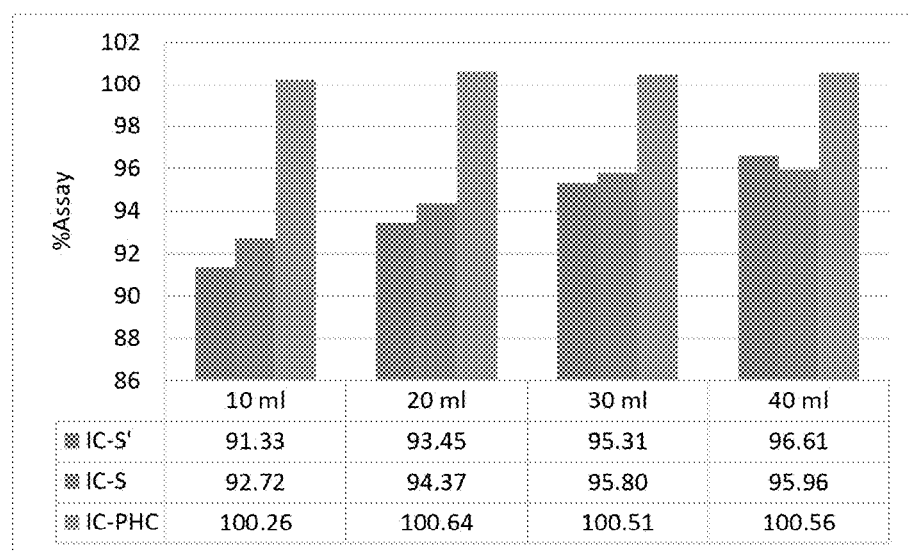
FIG. 6: Adsorption behaviour of Midazolam in different infusion containers at variable fill volume (Example 5)
IC-S' leftmost; IC-S center; IC-PHC rightmost

Example 5: Terminal Sterilization of Midazolam (1 mg/mL) Ready to Infuse Formulation Filled in IC-PHC Infusion Bag at Different Fill Volume Method: Adsorption behaviour of Midazolam in different bags (IC-S', IC-S and IC-PHC) was evaluated at four variable fill volumes, i.e. 10 ml, 20 ml, 30 ml and 40 ml. The assay values of autoclaved samples of Midazolam formulation were evaluated using an HPLC based assay method.
Results: Assay values of autoclaved sample of Midazolam in IC-S infusion bags showed increasing trend with increasing fill volume (FIG. 6). At lowest fill volume, surface area to volume ratio was high resulting higher adsorption of API on contact layer of infusion bags. As fill volume increases surface area to volume ratio decreases leads to lower adsorption and higher assay values. This confirmed the physical adsorption of Midazolam in IC-S infusion bags. Contrary, there was no impact of fill volume on potency of Midazolam in IC-PHC infusion bags. This also ruled out the possibility of Midazolam adsorption in IC-PHC infusion bags.

Figure 7:
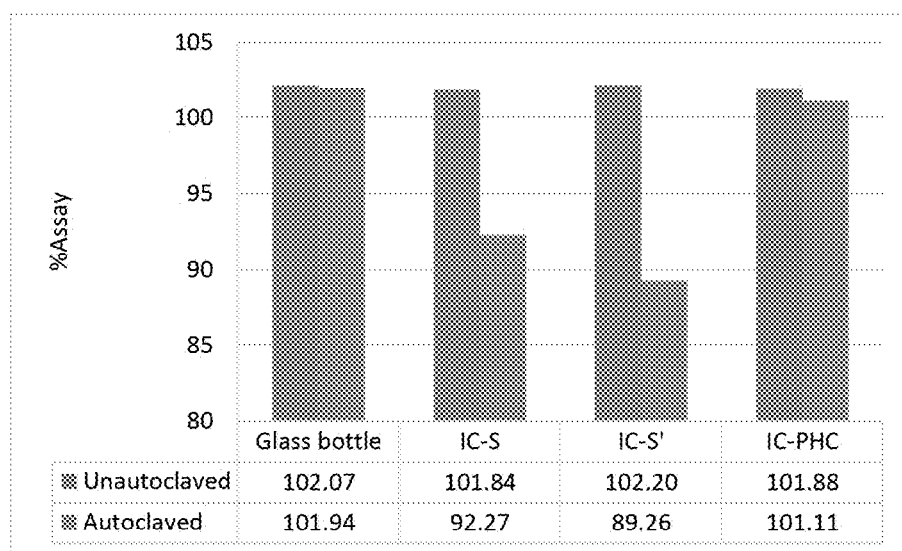
FIG. 7: Figure indicating no potency loss in IC-PHC infusion containers at lower concentration of 0.2 mg/mL (Example 6)
Unautoclaved on the left; autoclaved on the right
Figure 8:
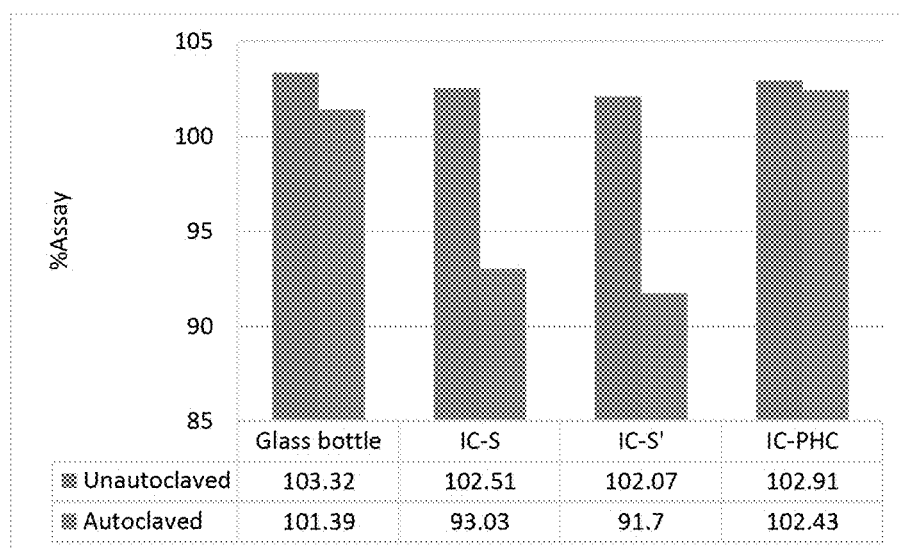
FIG. 8: Figure indicating no potency loss in IC-PHC infusion containers at lower concentration of 0.5 mg/mL (Example 6)
Unautoclaved on the left; autoclaved on the right
Figure 9:
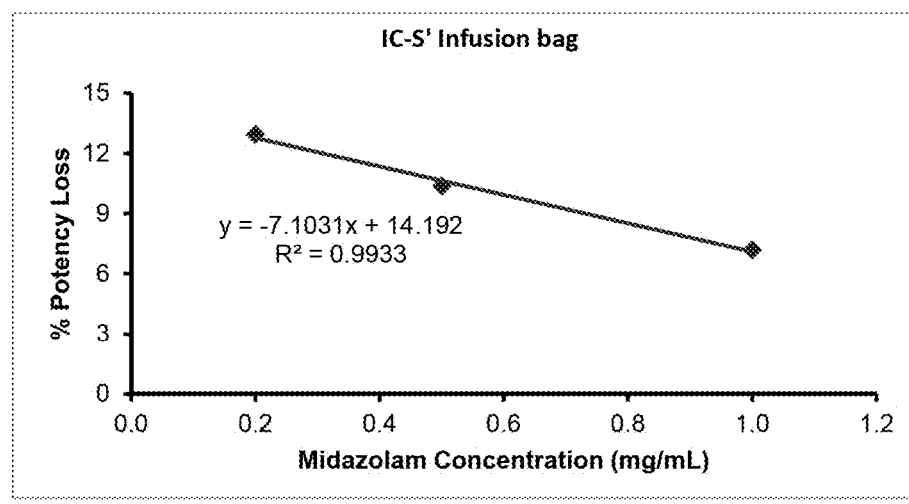
FIG. 9: Correlation between Midazolam concentration and potency loss in IC-S infusion containers (Example 6)

Example 6: Effect of Lower Concentration 0.2 and 0.5 mg/mL on Potency Loss in Different Infusion Bags Method: Loss of potency of Midazolam was assessed using an HPLC based assay method for (i) autoclaved and (ii) unautoclaved formulations (0.2 mg/ml and 0.5 mg/ml) in glass bottle, IC-S infusion bag, IC-S' infusion bag and IC-PHC infusion bag.
Discussion: FIGS. 7 and 8 shows potency loss in different infusion bags at lower concentration at 0.2 and 0.5 mg/mL respectively. The data showed significant potency loss in IC-S and IC-S' infusion bags whereas there was no potency loss found at lower concentration in IC-PHC infusion bags. As shown in FIG. 9, linear correlation exists between Midazolam concentration and potency loss ($r^2>0.99$) wherein with the decreasing concentration of Midazolam, potency loss increases linearly.

Example 7: Long Term Stability Data of Terminally Sterilized (Autoclaved) Midazolam Hydrochloride Formulation in IC-PHC Infusion Bags

TABLE 7

Stability data for Midazolam (1 mg/mL) in 0.9% sodium chloride injection @pH 3.0 in infusion bags

| Batch No | Stage | Packaging Specification | Stability Condition | Time points (M) | Assay - Midazolam 90-110% | Oxide Midazolam NMT 0.5% | 6-H Isomer NMT 0.5% | impurity H NMT 0.5% | impurity F NMT 0.5% |
|---|---|---|---|---|---|---|---|---|---|
| 26201282SB030 | Unautoclaved | IC-PHC | Initial | 0 | 102.03 | ND | ND | ND | ND |
|  | 1 time |  | Initial | 0 | 103.09 | ND | ND | ND | ND |
|  | autoclave |  | 25° C./40% RH | 1 | 101.31 | BQL | ND | ND | ND |
|  |  |  |  | 2 | 100.74 | BQL | ND | ND | BQL |
|  |  |  |  | 3 | 101.46 | ND | ND | ND | ND |
|  |  |  |  | 6 | 101.19 | BQL | ND | ND | BQL |
|  |  |  |  | 12 | 101.41 | BQL | ND | ND | ND |
|  |  |  |  | 18 | 101.22 | BQL | ND | ND | ND |

TABLE 7-continued

Stability data for Midazolam (1 mg/mL) in 0.9% sodium chloride injection @pH 3.0 in infusion bags

|  |  |  |  |  |  |  |  |
|---|---|---|---|---|---|---|---|
|  |  | 40° C./25% RH | 1 | 100.18 | BQL | ND | ND | ND |
|  |  |  | 2 | 100.42 | ND | ND | ND | ND |
|  |  |  | 3 | 101.82 | ND | ND | ND | BQL |
|  |  |  | 6 | 101.01 | BQL | ND | ND | BQL |
|  |  | 2-8 C. | 3 | 101.82 | ND | ND | ND | BQL |
|  |  |  | 6 | 100.80 | BQL | ND | ND | BQL |
|  |  |  | 12 | 100.68 | BQL | ND | ND | ND |

| Batch No | Stage | Packaging Specification | Stability Condition | Time points (M) | Midazolam Aldehyde Impurity NMT 0.5% | Highest Unknown NMT 0.1% | Total NMT 1% | pH — | Osmolality (mOsm/kg) 250-375 |
|---|---|---|---|---|---|---|---|---|---|
| 26201282SB030 | Unautoclaved | IC-PHC | Initial | 0 | BQL | ND | BQL | 3.12 | 296 |
|  | 1 time autoclave |  | Initial | 0 | 0.035 | BQL | 0.035 | 3.11 | 297 |
|  |  |  | 25° C./40% RH | 1 | 0.038 | ND | 0.038 | 3.13 | 298 |
|  |  |  |  | 2 | 0.037 | BQL | 0.037 | 3.15 | 296 |
|  |  |  |  | 3 | 0.039 | BQL | 0.039 | 3.14 | 289 |
|  |  |  |  | 6 | 0.035 | BQL | 0.035 | 3.13 | 295 |
|  |  |  |  | 12 | 0.037 | BQL | 0.037 | 3.18 | 297 |
|  |  |  |  | 18 | 0.046 | BQL | 0.046 | 3.17 | 293 |
|  |  |  | 40° C./25% RH | 1 | 0.040 | BQL | 0.040 | 3.13 | 296 |
|  |  |  |  | 2 | 0.039 | BQL | 0.039 | 3.14 | 298 |
|  |  |  |  | 3 | 0.040 | BQL | 0.040 | 3.14 | 289 |
|  |  |  |  | 6 | 0.040 | BQL | 0.040 | 3.13 | 295 |
|  |  |  | 2-8 C. | 3 | 0.034 | BQL | 0.034 | 3.12 | 289 |
|  |  |  |  | 6 | 0.033 | BQL | 0.033 | 3.13 | 294 |
|  |  |  |  | 12 | 0.037 | BQL | 0.037 | 3.18 | 298 |

ND: Not detected,
BQL: Below quantification limit,
LOQ: limit of quantification 0.032%.

TABLE 8

Stability data for Midazolam (1 mg/mL) in 0.9% sodium chloride injection @ pH 3.4 in infusion bags

| Batch No | Stage | Packaging Specification | Stability condition | Time points (M) | Assay - Midazolam 90-110% | Oxide Midazolam NMT 0.5% | 6-H Isomer NMT 0.5% | Impurity H NMT 0.5% | Impurity F NMT 0.5% |
|---|---|---|---|---|---|---|---|---|---|
| 26201282SB027 | Unautoclaved | IC-PHC | Initial | 0 | 101.76 | ND | ND | ND | ND |
|  | 1 time autoclave |  | Initial | 0 | 100.88 | ND | ND | ND | ND |
|  |  |  | 25° C./40% RH | 1 | 101.99 | ND | ND | ND | BQL |
|  |  |  |  | 3 | 101.01 | ND | ND | ND | BQL |
|  |  |  |  | 6 | 101.13 | ND | ND | ND | ND |
|  |  |  |  | 12 | 100.98 | ND | ND | ND | ND |
|  |  |  |  | 18 | 99.57 | ND | BQL | BQL | BQL |
|  |  |  | 40° C./25% RH | 1 | 101.42 | ND | ND | ND | BQL |
|  |  |  |  | 2 | 100.44 | ND | ND | ND | BQL |
|  |  |  |  | 3 | 101.18 | ND | ND | ND | ND |
|  |  |  |  | 6 | 101.19 | BQL | ND | ND | ND |
|  |  |  | 2-8 C. | 3 | 100.73 | ND | ND | ND | BQL |
|  |  |  |  | 6 | 101.01 | ND | ND | ND | ND |

| Batch No | Stage | Packaging Specification | Stability condition | Time points (M) | Midazolam Aldehyde Impurity NMT 0.5% | Highest Unknown NMT 0.1% | Total NMT 1% | pH 3.0-4.5 | Osmolality (mOsm/kg) 250-375 |
|---|---|---|---|---|---|---|---|---|---|
| 26201282SB027 | Unautoclaved | IC-PHC | Initial | 0 | BQL | ND | BQL | 3.42 | 294 |
|  | 1 time autoclave |  | Initial | 0 | 0.032 | ND | 0.032 | 3.41 | 295 |
|  |  |  | 25° C./40% RH | 1 | 0.032 | BQL | 0.032 | 3.41 | 294 |
|  |  |  |  | 3 | 0.032 | BQL | 0.032 | 3.41 | 294 |
|  |  |  |  | 6 | 0.036 | ND | 0.036 | 3.39 | 294 |
|  |  |  |  | 12 | 0.036 | BQL | 0.036 | 3.42 | 296 |
|  |  |  |  | 18 | 0.043 | BQL | 0.043 | 3.40 | 290 |
|  |  |  | 40° C./25% RH | 1 | 0.037 | BQL | 0.037 | 3.42 | 299 |
|  |  |  |  | 2 | 0.036 | BQL | 0.036 | 3.36 | 295 |
|  |  |  |  | 3 | 0.042 | BQL | 0.042 | 3.42 | 295 |
|  |  |  |  | 6 | 0.047 | ND | 0.047 | 3.41 | 295 |
|  |  |  | 2-8 C. | 3 | 0.036 | BQL | 0.036 | 3.38 | 296 |
|  |  |  |  | 6 | 0.032 | ND | 0.032 | 3.42 | 294 |

ND: Not detected,
BQL: Below quantification limit,
LOQ: limit of quantification 0.032%.

TABLE 9

Stability data for Midazolam (0.5 mg/mL) in 0.9% sodium chloride injection @pH 3.4 in infusion bags

| Batch No | Stage | Packaging Specification | Stability condition | Time points (M) | Assay - Midazolam 90-110% | Oxide Midazolam NMT 0.5% | 6-H Isomer NMT 0.5% | Impurity H NMT 0.5% | Impurity F NMT 0.5% |
|---|---|---|---|---|---|---|---|---|---|
| 26201282SB028 | Unautoclaved | IC-PHC | Initial | 0 | 101.55 | ND | ND | ND | ND |
|  | 1 time autoclave |  | Initial | 0 | 101.06 | ND | ND | ND | ND |
|  |  |  | 25° C./40% RH | 1 | 102.67 | BQL | ND | ND | ND |
|  |  |  |  | 2 | 100.08 | ND | ND | ND | ND |
|  |  |  |  | 3 | 100.92 | ND | ND | ND | ND |
|  |  |  |  | 6 | 101.83 | BQL | ND | ND | ND |
|  |  |  |  | 20 | 103.14 | ND | ND | BQL | ND |
|  |  |  | 40° C./25% RH | 1 | 101.77 | BQL | ND | ND | ND |
|  |  |  |  | 2 | 101.09 | ND | ND | ND | ND |
|  |  |  |  | 3 | 101.01 | ND | ND | ND | ND |
|  |  |  |  | 6 | 101.34 | BQL | ND | ND | ND |
|  |  |  | 2-8° C. | 6 | 101.87 | BQL | ND | ND | ND |
|  |  |  |  | 12 | 102.32 | BQL | BQL | BQL | BQL |

| Batch No | Stage | Packaging Specification | Stability condition | Time points (M) | Midazolam Aldehyde Impurity NMT 0.5% | Highest Unknown NMT 0.1% | Total NMT 1% | pH 3.0-4.5 | Osmolality (mOsm/kg) 250-375 |
|---|---|---|---|---|---|---|---|---|---|
| 26201282SB028 | Unautoclaved | IC-PHC | Initial | 0 | BQL | BQL | BQL | 3.40 | 296 |
|  | 1 time autoclave |  | Initial | 0 | 0.035 | BQL | 0.035 | 3.39 | 296 |
|  |  |  | 25° C./40% RH | 1 | 0.039 | ND | 0.039 | 3.44 | 300 |
|  |  |  |  | 2 | 0.045 | ND | 0.045 | 3.44 | 296 |
|  |  |  |  | 3 | 0.033 | ND | 0.033 | 3.34 | 295 |
|  |  |  |  | 6 | 0.052 | ND | 0.052 | 3.33 | 292 |
|  |  |  |  | 20 | 0.054 | BQL | 0.054 | 3.35 | 291 |
|  |  |  | 40° C./25% RH | 1 | 0.050 | BQL | 0.050 | 3.34 | 287 |
|  |  |  |  | 2 | 0.051 | ND | 0.051 | 3.42 | 296 |
|  |  |  |  | 3 | 0.047 | ND | 0.047 | 3.38 | 300 |
|  |  |  |  | 6 | 0.057 | BQL | 0.057 | 3.34 | 293 |
|  |  |  | 2-8° C. | 6 | 0.042 | ND | 0.042 | 3.35 | 293 |
|  |  |  |  | 12 | 0.092 | BQL | 0.092 | 3.40 | 294 |

ND: Not detected,
BQL: Below quantification limit,
LOQ: limit of quantification 0.032%.

TABLE 10

Stability data for Midazolam (1 mg/mL) in 0.9% sodium chloride injection @pH 3.4 in infusion bags

| Batch No | Stage | Packaging Specification | Stability Condition | Time points (M) | Assay - Midazolam 90-110% | Oxide Midazolam NMT 0.5% | 6-H Isomer NMT 0.5% | Impurity H NMT 0.5% | Impurity F NMT 0.5% |
|---|---|---|---|---|---|---|---|---|---|
| 26201282SB032 | Unautoclaved | IC-PHC | Initial | 0 | 98.96 | ND | ND | ND | ND |
|  | 1 time autoclave |  | Initial | 0 | 98.80 | ND | ND | ND | BQL |
|  |  |  | 25° C./40% RH | 1 | 99.84 | BQL | BQL | ND | ND |
|  |  |  |  | 2 | 100.03 | BQL | ND | ND | BQL |
|  |  |  |  | 3 | 100.59 | BQL | ND | ND | ND |
|  |  |  |  | 6 | 101.50 | BQL | ND | ND | BQL |
|  |  |  |  | 12 | 100.87 | BQL | BQL | BQL | ND |
|  |  |  |  | 18 | 100.67 | BQL | ND | ND | ND |
|  |  |  | 40° C./25% RH | 1 | 99.84 | BQL | BQL | ND | ND |
|  |  |  |  | 2 | 99.28 | ND | ND | ND | ND |
|  |  |  |  | 3 | 100.18 | ND | ND | ND | ND |
|  |  |  |  | 6 | 101.31 | BQL | ND | ND | BQL |
|  |  |  | 2-8 C. | 3 | 100.98 | BQL | ND | ND | ND |
|  |  |  |  | 6 | 100.96 | BQL | ND | ND | BQL |
|  |  |  |  | 12 | 101.07 | BQL | ND | BQL | BQL |

TABLE 10-continued

Stability data for Midazolam (1 mg/mL) in 0.9% sodium chloride injection @pH 3.4 in infusion bags

| Batch No | Stage | Packaging Specification | Stability Condition | Time points (M) | Midazolam Aldehyde Impurity NMT 0.5% | Highest Unknown NMT 0.1% | Total NMT 1% | pH 3.0-4.5 | Osmolality (mOsm/kg) 250-375 |
|---|---|---|---|---|---|---|---|---|---|
| 26201282SB032 | Unautoclaved | IC-PHC | Initial | 0 | 0.037 | ND | 0.037 | 3.35 | 299 |
| | 1 time | | Initial | 0 | 0.051 | BQL | 0.051 | 3.36 | 301 |
| | autoclave | | 25° C./40% RH | 1 | 0.055 | ND | 0.055 | 3.36 | 299 |
| | | | | 2 | 0.053 | BQL | 0.053 | 3.37 | 300 |
| | | | | 3 | 0.052 | BQL | 0.052 | 3.36 | 293 |
| | | | | 6 | 0.051 | BQL | 0.051 | 3.37 | 296 |
| | | | | 12 | 0.055 | BQL | 0.055 | 3.38 | 299 |
| | | | | 18 | 0.067 | BQL | 0.067 | 3.35 | 295 |
| | | | 40° C./25% RH | 1 | 0.053 | ND | 0.053 | 3.33 | 299 |
| | | | | 2 | 0.057 | BQL | 0.057 | 3.36 | 303 |
| | | | | 3 | 0.063 | BQL | 0.063 | 3.36 | 298 |
| | | | | 6 | 0.069 | BQL | 0.069 | 3.36 | 300 |
| | | | 2-8 C. | 3 | 0.059 | ND | 0.059 | 3.35 | 291 |
| | | | | 6 | 0.050 | BQL | 0.050 | 3.37 | 297 |
| | | | | 12 | 0.054 | BQL | 0.054 | 3.39 | 301 |

ND: Not detected,
BQL: Below quantification limit,
LOQ: limit of quantification 0.032%.

TABLE 11

Stability data for Midazolam (1 mg/mL) in 0.9% sodium chloride injection @pH 3.7 in PHC infusion bags

| Batch No | Stage | Packaging Specification | Stability Condition | Time points (M) | Assay - Midazolam 90-110% | Oxide Midazolam NMT 0.5% | 6-H Isomer NMT 0.5% | Impurity H NMT 0.5% | Impurity F NMT 0.5% |
|---|---|---|---|---|---|---|---|---|---|
| 26201282SB031 | Unautoclaved | IC-PHC | Initial | 0 | 100.13 | ND | ND | ND | ND |
| | 1 time autoclave | | Initial | 0 | 99.16 | ND | ND | ND | BQL |
| | | | 25° C./40% RH | 1 | 100.69 | BQL | ND | ND | ND |
| | | | | 2 | 101.07 | ND | ND | ND | ND |
| | | | | 3 | 101.89 | ND | ND | ND | BQL |
| | | | | 6 | 100.69 | BQL | ND | ND | BQL |
| | | | | 12 | 100.65 | BQL | ND | BQL | BQL |
| | | | | 18 | 101.06 | BQL | ND | ND | ND |
| | | | 40° C./25% RH | 1 | 100.50 | BQL | BQL | ND | ND |
| | | | | 2 | 100.11 | ND | ND | ND | BQL |
| | | | | 3 | 101.19 | ND | ND | ND | BQL |
| | | | | 6 | 100.82 | BQL | ND | ND | BQL |
| | | | 2-8 C. | 3 | 101.80 | ND | ND | ND | BQL |
| | | | | 6 | 100.53 | BQL | ND | ND | BQL |
| | | | | 12 | 100.92 | BQL | ND | ND | ND |

| Batch No | Stage | Packaging Specification | Stability Condition | Time points (M) | Midazolam Aldehyde Impurity NMT 0.5% | Highest Unknown NMT 0.1% | Total NMT 1% | pH — | Osmolality (mOsm/kg) 250-375 |
|---|---|---|---|---|---|---|---|---|---|
| 26201282SB031 | Unautoclaved | IC-PHC | Initial | 0 | BQL | ND | BQL | 3.83 | 299 |
| | 1 time autoclave | | Initial | 0 | BQL | BQL | BQL | 3.83 | 300 |
| | | | 25° C./40% RH | 1 | BQL | BQL | BQL | 3.81 | 299 |
| | | | | 2 | BQL | BQL | BQL | 3.83 | 300 |
| | | | | 3 | BQL | BQL | BQL | 3.82 | 290 |
| | | | | 6 | BQL | BQL | BQL | 3.83 | 297 |
| | | | | 12 | 0.032 | BQL | 0.032 | 3.84 | 298 |
| | | | | 18 | 0.034 | BQL | 0.034 | 3.72 | 295 |
| | | | 40° C./25% RH | 1 | 0.032 | ND | 0.032 | 3.89 | 299 |
| | | | | 2 | 0.032 | BQL | 0.032 | 3.82 | 298 |
| | | | | 3 | BQL | BQL | BQL | 3.84 | 291 |
| | | | | 6 | 0.031 | BQL | 0.031 | 3.82 | 297 |
| | | | 2-8 C. | 3 | BQL | BQL | BQL | 3.80 | 290 |
| | | | | 6 | BQL | BQL | BQL | 3.80 | 296 |
| | | | | 12 | BQL | BQL | BQL | 3.87 | 300 |

ND: Not detected,
BQL: Below quantification limit,
LOQ: limit of quantification 0.032%.

TABLE 12

Stability data for Midazolam (1 mg/mL) in 0.9% sodium chloride injection @pH 4 in IC-PHC infusion bags

| Batch No | Stage | Packaging Specification | Stability Condition | Time points (Month) | Assay - Midazolam 90-110% | Oxide Midazolam NMT 0.5% | 6-H Isomer NMT 0.5% | impurity H NMT 0.5% | impurity F NMT 0.5% |
|---|---|---|---|---|---|---|---|---|---|
| 26201282PF027 | Unautoclaved 1 time autoclave | IC-PHC | Unautoclaved Initial | 0 | 100.56 | ND | ND | ND | ND |
| | | | | 0 | 100.77 | ND | ND | ND | ND |
| | | | 25° C./40% RH | 1 | 101.35 | ND | ND | ND | ND |
| | | | | 2 | 101.35 | ND | ND | ND | ND |
| | | | | 3 | 101.26 | ND | ND | ND | ND |
| | | | | 6 | 101.82 | BQL | ND | ND | BQL |
| | | | | 12 | 101.22 | BQL | BQL | ND | ND |
| | | | 40° C./25% RH | 1 | 101.26 | ND | ND | ND | ND |
| | | | | 2 | 101.35 | ND | ND | ND | ND |
| | | | | 3 | 101.75 | ND | ND | ND | ND |
| | | | | 6 | 100.99 | BQL | BQL | ND | BQL |
| | | | 2-8 C. | 1 | 102.70 | ND | BQL | ND | ND |
| | | | | 2 | 101.75 | ND | ND | ND | ND |
| | | | | 3 | 101.63 | ND | ND | ND | ND |
| | | | | 6 | 101.76 | ND | ND | ND | ND |

| Batch No | Stage | Packaging Specification | Stability Condition | Time points (Month) | Midazolam Aldehyde Impurity NMT 0.5% | Highest Unknown NMT 0.1% | Total NMT 1% | pH — | Osmolality (mOsm/kg) 250-375 |
|---|---|---|---|---|---|---|---|---|---|
| 26201282PF027 | Unautoclaved 1 time autoclave | IC-PHC | Unautoclaved Initial | 0 | BQL | ND | BQL | 4.08 | 299 |
| | | | | 0 | BQL | ND | BQL | 4.07 | 296 |
| | | | 25° C./40% RH | 1 | BQL | BQL | BQL | 4.09 | 298 |
| | | | | 2 | BQL | ND | BQL | 4.07 | 298 |
| | | | | 3 | BQL | BQL | BQL | 3.95 | 288 |
| | | | | 6 | BQL | BQL | BQL | 4.06 | 295 |
| | | | | 12 | BQL | BQL | BQL | 4.05 | 297 |
| | | | 40° C./25% RH | 1 | BQL | ND | BQL | 4.16 | 297 |
| | | | | 2 | BQL | ND | BQL | 4.07 | 298 |
| | | | | 3 | BQL | BQL | BQL | 3.95 | 289 |
| | | | | 6 | 0.035 | BQL | 0.035 | 4.01 | 297 |
| | | | 2-8 C. | 1 | BQL | ND | BQL | 4.05 | 298 |
| | | | | 2 | BQL | ND | BQL | 4.23 | 307 |
| | | | | 3 | BQL | BQL | BQL | 3.97 | 290 |
| | | | | 6 | BQL | BQL | BQL | 4.04 | 295 |

ND: Not detected,
BQL: Below quantification limit,
LOQ: limit of quantification 0.032%.

TABLE 13

Stability data for Midazolam (1 mg/mL) in 0.9% sodium chloride injection @pH 4.3 in IC-PHC infusion bags

| Batch No | Stage | Packaging Specification | Stability Condition | Time points (Month) | Assay - Midazolam 90-110% | Oxide Midazolam NMT 0.5% | 6-H Isomer NMT 0.5% | impurity H NMT 0.5% | impurity F NMT 0.5% |
|---|---|---|---|---|---|---|---|---|---|
| 26201282PF038 | Unautoclaved 1 time autoclave | IC-PHC | Unautoclaved Initial | Initial | 100.96 | ND | ND | ND | ND |
| | | | | Initial | 100.85 | BQL | ND | ND | BQL |
| | | | 25° C./40% RH | 1 | 100.67 | BQL | ND | ND | BQL |
| | | | | 2 | 100.63 | BQL | ND | ND | BQL |
| | | | | 3 | 101.84 | BQL | BQL | BQL | BQL |
| | | | | 6 | 101.68 | BQL | BQL | BQL | BQL |
| | | | | 12 | 99.29 | BQL | BQL | ND | BQL |
| | | | 40° C./25% RH | 1 | 100.47 | BQL | ND | ND | BQL |
| | | | | 2 | 100.27 | BQL | ND | ND | BQL |
| | | | | 3 | 101.45 | BQL | BQL | BQL | BQL |
| | | | | 6 | 101.39 | BQL | BQL | ND | BQL |

TABLE 13-continued

Stability data for Midazolam (1 mg/mL) in 0.9% sodium chloride injection @pH 4.3 in IC-PHC infusion bags

| Batch No | Stage | Packaging Specification | Stability Condition | Time points (Month) | Midazolam Aldehyde Impurity NMT 0.5% | Highest Unknown NMT 0.1% | Total (%) NMT 1% | pH | Osmolality (mOsm/kg) 250-375 |
|---|---|---|---|---|---|---|---|---|---|
| 26201282PF038 | Unautoclaved | — | Unautoclaved | Initial | 0.038 | BQL | 0.038 | 4.25 | 302 |
| | 1 time autoclave | IC-PHC | Initial | Initial | 0.046 | BQL | 0.046 | 4.23 | 302 |
| | | | 25° C./40% RH | 1 | 0.046 | BQL | 0.046 | 4.27 | 301 |
| | | | | 2 | 0.042 | BQL | 0.042 | 4.35 | 303 |
| | | | | 3 | 0.051 | BQL | 0.051 | 4.22 | 300 |
| | | | | 6 | 0.057 | BQL | 0.057 | 4.25 | 302 |
| | | | | 12 | 0.045 | BQL | 0.045 | 4.25 | 304 |
| | | | 40° C./25% RH | 1 | 0.046 | BQL | 0.046 | 4.26 | 303 |
| | | | | 2 | 0.048 | BQL | 0.048 | 4.27 | 303 |
| | | | | 3 | 0.059 | BQL | 0.059 | 4.19 | 302 |
| | | | | 6 | 0.065 | BQL | 0.065 | 4.19 | 302 |

ND: Not detected,
BQL: Below quantification limit,
LOQ: limit of quantification 0.032%

TABLE 14

Stability data for Midazolam (1 mg/mL) in 0.9% sodium chloride injection @pH 4.5 in IC-PHC infusion bags

| Batch No | Stage | Packaging Specification | Stability Condition | Time points (Month) | Assay - Midazolam 90-110% | Oxide Midazolam NMT 0.5% | 6-H Isomer NMT 0.5% | impurity H NMT 0.5% | impurity F NMT 0.5% |
|---|---|---|---|---|---|---|---|---|---|
| 26201282PF039 | Unautoclaved | — | Unautoclaved | 0 | 101.12 | ND | ND | ND | ND |
| | 1 time autoclave | IC-PHC | Initial | 0 | 100.84 | BQL | ND | BQL | BQL |
| | | | 25° C./40% RH | 1 | 101.28 | BQL | BQL | ND | BQL |
| | | | | 2 | 101.53 | BQL | BQL | ND | BQL |
| | | | | 3 | 103.35 | BQL | BQL | BQL | BQL |
| | | | | 6 | 100.78 | BQL | BQL | ND | BQL |
| | | | | 12 | 98.88 | BQL | BQL | ND | BQL |
| | | | 40° C./25% RH | 1 | 101.03 | BQL | BQL | ND | BQL |
| | | | | 2 | 101.27 | BQL | BQL | BQL | BQL |
| | | | | 3 | 102.76 | BQL | BQL | BQL | BQL |
| | | | | 6 | 100.85 | BQL | BQL | ND | BQL |

| Batch No | Stage | Packaging Specification | Stability Condition | Time points (Month) | Midazolam Aldehyde Impurity NMT 0.5% | Highest Unknown NMT 0.1% | Total (%) NMT 1% | pH | Osmolality (mOsm/kg) 250-375 |
|---|---|---|---|---|---|---|---|---|---|
| 26201282PF039 | Unautoclaved | — | Unautoclaved | 0 | BQL | BQL | BQL | 4.45 | 301 |
| | 1 time autoclave | IC-PHC | Initial | 0 | BQL | BQL | BQL | 4.44 | 303 |
| | | | 25° C./40% RH | 1 | BQL | BQL | BQL | 4.43 | 299 |
| | | | | 2 | BQL | BQL | BQL | 4.49 | 301 |
| | | | | 3 | 0.032 | BQL | 0.032 | 4.38 | 300 |
| | | | | 6 | 0.033 | BQL | 0.033 | 4.40 | 303 |
| | | | | 12 | BQL | BQL | BQL | 4.28 | 302 |
| | | | 40° C./25% RH | 1 | 0.030 | BQL | 0.030 | 4.44 | 300 |
| | | | | 2 | 0.030 | BQL | 0.030 | 4.46 | 300 |
| | | | | 3 | 0.039 | BQL | 0.039 | 4.42 | 299 |
| | | | | 6 | 0.050 | BQL | 0.050 | 4.35 | 303 |

ND: Not detected,
BQL: Below quantification limit,
LOQ: limit of quantification 0.032%

Results: It is clearly evident from the above long term storage stability data that there is no change in any of the critical quality attributes (CQAs) in long term and accelerated stability conditions between pH 3.0 to 4.5, thereby suggesting long term storage stability of infusion bags comprising ready-to-infuse, terminally sterilized, aqueous formulation of Midazolam hydrochloride at pH range of 3.0 to 4.5. Therefore, it can be presumed that Midazolam hydrochloride infusion bags according to the present invention will remain stable in the range 3 to 4.5, preferably 3.0 to 4.0 and more preferably 3.4±0.2.

We claim:
1. A sterile, ready-to-use infusion container comprising a stable,
aqueous solution of midazolam comprising:
 a. midazolam or a pharmaceutically acceptable salt thereof;
 b. a tonicity adjusting agent;
 c. a pH adjusting agent; and
 d. water for injection,
wherein the midazolam or pharmaceutically acceptable salt thereof does not adsorb on an innermost layer of the infusion container, the innermost layer is made-up of a cyclo-olefin polymer or a cyclo-olefin co-polymer, and the solution was subjected to terminal sterilization by autoclaving.

2. The sterile, ready-to-use infusion container according to claim 1, wherein the stable, aqueous solution has a concentration of 0.1 mg/ml to 2.0 mg/ml of midazolam or a base equivalent concentration of a pharmaceutically acceptable salt thereof.

3. The sterile, ready-to-use infusion container according to claim 1, wherein the stable, aqueous solution has a concentration of 0.5 mg/ml to 1.0 mg/ml of midazolam or a base equivalent concentration of a pharmaceutically acceptable salt thereof.

4. The sterile, ready-to-use infusion container according to claim 1, wherein the tonicity adjusting agent is sodium chloride.

5. The sterile, ready-to-use infusion container according to claim 1, wherein the pH of the stable, aqueous solution is 3.0 to 4.5.

6. The sterile, ready-to-use infusion container according to claim 1, wherein the pH of the stable, aqueous solution is 3.0 to 4.0.

7. The sterile, ready-to-use infusion container according to claim 1, wherein the pH of the stable, aqueous solution is 3.4±0.2.

8. The sterile, ready-to-use infusion container according to claim 1, wherein the stable aqueous solution is free of a chelating agent, an antioxidant, a stabilizer, a complexing agent and/or a preservative.

9. The sterile, ready-to-use infusion container according to claim 1, wherein the container is a rigid, semi-rigid or a flexible container.

10. The sterile, ready-to-use infusion container according to claim 1, wherein the container is a flexible bag.

11. The sterile, ready-to-use flexible bag according to claim 10, wherein the wall of the body of the bag comprises at least two layers and wherein the innermost layer is made-up of a material that does not show adsorption of midazolam on its surface.

12. The sterile, ready-to-use flexible bag according to claim 10, wherein the wall of the body of the flexible infusion bag comprises at least three layers wherein the outermost layer is made-up of polypropylene (PP), middle layer is made-up of linear low density polyethylene (LL-DPE), and the innermost layer is made-up of a cyclo-olefin polymer or a cyclo-olefin co-polymer.

13. The sterile, ready-to-use, infusion container according to claim 1, wherein the container is terminally sterilized.

14. The sterile, ready-to-use, infusion container according to claim 1, wherein the container is optionally overwrapped by an overwrap pouch covering the filled and sealed infusion container.

15. A sterile, ready-to-use infusion container comprising a stable,
aqueous solution of midazolam comprising:
a. midazolam or a pharmaceutically acceptable salt thereof;
b. a tonicity adjusting agent;
c. a pH adjusting agent; and
d. water for injection,
wherein (i) the aqueous solution of midazolam of a pharmaceutically acceptable salt thereof in the container remains free of any sub-visible particles (Nylon particles) at room temperature for at least 6 months (ii) the innermost layer of the infusion container is made-up of a cyclo-olefin polymer or a cyclo-olefin co-polymer, and (iii) the solution was subjected to terminal sterilization by autoclaving.

16. The sterile, ready-to-use infusion container according to claim 1, wherein the infusion container is a flexible, multi-layered bag comprising:
a, a body filled with about 80 ml to about 500 ml of the stable, aqueous solution of midazolam or a pharmaceutically acceptable salt thereof; and
b. one or more tubes fixed to the body of the infusion bag.

17. The sterile, ready-to-use, infusion container according to claim 1, wherein the container comprises at least two tubes with one of the at least two tubes fixed to the body of the infusion bag, and wherein one of the at least two tubes is fitted to an outlet port which is designed to attach to a sterile infusion set, and another tube is fitted to an inlet port which is designed to receive a sterile fluid which is with or without a medicament other than midazolam.

18. A method of treating a disease or a condition or providing a supportive medication comprising intravenously administering to a patient in need thereof, a stable, aqueous solution of midazolam or a pharmaceutically acceptable salt thereof from an infusion container according to claim 1.

19. The method according to claim 18, wherein the disease or condition for treatment or supportive medication is selected from the group consisting of preoperative sedation, anxiolysis, amnesia, for induction of general anaesthesia and before administration of other anaesthetics agents.

* * * * *